United States Patent [19]

Hittich et al.

[11] Patent Number: 4,693,841
[45] Date of Patent: Sep. 15, 1987

[54] CARBONITRILES

[75] Inventors: Reinhard Hittich, Modautal; Georg Weber, Erzhausen; Wolfgang Sucrow; Peter Geschwinder, both of Paderborn, all of Fed. Rep. of Germany

[73] Assignee: Merck Patent Gesellschaft mit Beschrankter Haftung, Darmstadt, Fed. Rep. of Germany

[21] Appl. No.: 802,888

[22] Filed: Nov. 29, 1985

[30] Foreign Application Priority Data

Dec. 1, 1984 [DE] Fed. Rep. of Germany ....... 3443929

[51] Int. Cl.$^4$ .................. C09K 3/34; C09K 19/32; C07C 121/46; C07C 121/48
[52] U.S. Cl. ..................... 252/299.62; 252/299.5; 252/299.63; 350/350 R; 558/429
[58] Field of Search ............... 252/299.62, 299.63, 252/299.5; 260/464; 350/350 R, 350 S; 558/429

[56] References Cited

U.S. PATENT DOCUMENTS

| | | | |
|---|---|---|---|
| 4,391,731 | 7/1983 | Boller et al. | 252/299.62 |
| 4,421,670 | 12/1983 | Deutscher et al. | 252/299.62 |
| 4,432,885 | 2/1984 | Petrzilka et al. | 252/299.62 |
| 4,434,073 | 2/1984 | Sucrow et al. | 252/299.62 |
| 4,510,069 | 4/1985 | Eidenschink et al. | 252/299.62 |
| 4,600,528 | 7/1986 | Eidenschink et al. | 252/299.62 |

FOREIGN PATENT DOCUMENTS

| | | | |
|---|---|---|---|
| 127816 | 12/1984 | European Pat. Off. | 252/299.62 |
| 2747113 | 4/1979 | Fed. Rep. of Germany | 252/299.63 |
| 3522023 | 1/1986 | Fed. Rep. of Germany | 252/299.62 |
| 210920 | 6/1984 | German Democratic Rep. | 252/299.62 |

OTHER PUBLICATIONS

Pfenninger, J., et al., Helv. Chim. Acta., vol. 63(6), pp. 1562–1581, (1980).
Varech, D., et al., Nouv. J. Chim., vol. 8, No. 7, pp. 445–452, (1984).
Sucrow, W., et al., Chem. Ber., vol. 118, No. 8, pp. 3332–3349, (1985).

Primary Examiner—Teddy S. Gron
Attorney, Agent, or Firm—Millen & White

[57] ABSTRACT

Carbonitriles of the formula I

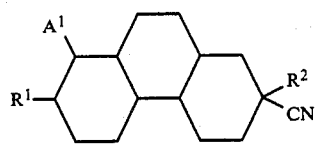

wherein
$R^1$ and $R^2$ are each an alkyl group having 1–12 C atoms and wherein one or two $CH_2$ groups/can be groups which are not adjacent replaced by —O—, —O—CO—, —CO—O— and/or —CH=CH—, and
$A^1$ is a H or

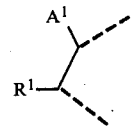

is a group of the formula 1

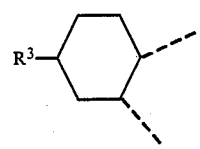

(1)

wherein
$R^3$ has one of the meanings of $R^1$, can be used as components of liquid crystal phases.

17 Claims, No Drawings

CARBONITRILES

This invention relates to new carbonitriles.

SUMMARY OF THE INVENTION

It is an object of this invention to provide new stable liquid crystal or mesogenic compound which are suitable for use as components of liquid crystal phases.

Upon further study of the specification and appended claims, further objects and advantages of this invention will become apparent to those skilled in the art.

These objects have been achieved by providing new carbonitriles of formula I

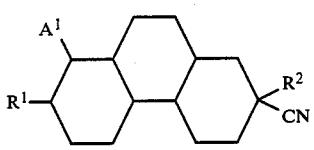

wherein
$R^1$ and $R^2$ are each an alkyl group having 1–12 C atoms and wherein one or two $CH_2$ groups which are not adjacent can be replaced by —O—, —O—CO—, —CO—O— and/or —CH=CH—, and
$A^1$ is H or

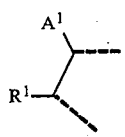

is a group of the formula 1

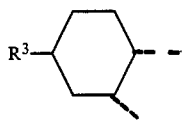

wherein
$R^3$ has one of the meanings of $R^1$.

DETAILED DISCUSSION

Similar compounds have been disclosed, for example, in German Offenlegungsschrift No. 3,319,781.

Like similar compounds, the compounds of the formula I can be used as components of liquid crystal phases, in particular for displays based on the principle of the twisted cell, the guest-host effect, the effect of deformation of aligned phases or the effect of dynamic scattering.

It has been found that the compounds of the formula I are excellently suitable for use as components of liquid crystal phases. In particular, it is possible to prepare by means of them stable liquid crystal phases having strongly negative dielectric anisotropy and hence electrooptical effects of low threshold or control voltage, very low optical anisotropy, comparatively low viscosity and relatively high clear points.

In addition, the range of liquid crystal substances which are suitable from various aspects of technical performance in use for the preparation of nematic mixtures is considerably enlarged, in a very general way, by the provision of the compounds of the formula I.

The compounds of the formula I have a wide field of use. Depending on the selection of the substituents, these compounds can be used as the base materials of which liquid crystal phases are predominantly composed; it is also possible, however, to add compounds of the formula I to liquid crystal base materials composed of other classes of compounds in order, for example, to affect the dielectric and/or optional anisotropy or the clear point of a dielectric of this type. The compounds of formula I are also suitable for use as intermediate products for the preparation of other substances which can be used as constituents of liquid crystal phases.

The compounds of the formula I are colorless in the pure state and form liquid crystal meso-phases within a temperature range advantageously situated for electro-optical use. They are very stable to chemicals, heat and light.

The invention relates, therefore, to the compounds of the formula I and to a process for their preparation, characterized in that a compound of the formula I wherein $R^2$ is H is reacted with a compound of the formula II $$R^2-X \qquad \qquad II$$

wherein
X is Cl, Br, I, OH or a reactive esterified OH group and $R^2$ has the meaning indicated.

The invention also relates to the use of the compounds of the formula I as components of liquid crystal phases. The invention also relates to liquid crystal phases containing at least one compound of the formula I and also to liquid crystal display elements, in particular electrooptical display elements, containing phases of this type.

Accordingly, the compounds of the formula I embrace perhydrophenanthrene derivatives of the partial formula Ia and perhydrochrysene derivatives of the partial formula Ib:

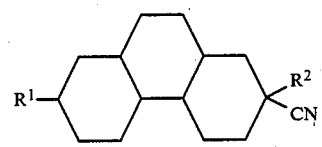

In the compounds of the formulae above and below, $R^1$ and $R^3$ are preferably alkyl, and also alkoxy or another oxaalkyl group. $R^2$ is preferably alkyl.

X is preferably Cl or Br, but also I, OH or reactive esterified OH, such as alkylsulfonyloxy having, in particular, 1–6 C atoms (for example methylsulfonyloxy) or arylsulfonyloxy having, in particular, 6–10 C atoms (for example phenylsulfonyloxy, p-tolylsulfonyloxy or naphthylsulfonyloxy).

In the compounds of the formulae above and below, the alkyl radicals, in which one (alkoxy or oxaalkyl) or two (alkoxyalkoxy or dioxyalkyl) non-adjacent $CH_2$ groups can be replaced by O atoms, are linear or branched. They are preferably linear and have 2, 3, 4, 5, 6 or 7 C atoms accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2-oxa-butyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5-, or 3,5-dioxahexyl or 1,3-, 1,4-, 1,5-, 1,6-, 2,4-, 2,5-, 2,6-, 3,5-, 3,6- or 4,6-dioxaheptyl.

If one or two $CH_2$ groups in the alkyl radicals of the formulae above and below are replaced by —CH=CH—, the trans-alkylene groups are preferred. These alkylene groups can thus contain 1 to 13 C atoms (or 14 C atoms in the case of dienyl groups).

Compounds of the formula I and also Ia and Ib containing branched wing groups $R^1$, $R^2$ or $R^3$ can in certain cases be of importance because of improved solubility in the customary liquid crystal base materials, but especially as chiral doping substances, if they are optically active. As a rule, branched groups of this type contain not more than one chain branching. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Preferred compounds among the compounds of the formulae I and also Ia and Ib are those in which at least one of the radicals contained therein has one of the preferred meanings indicated. Smaller and particularly preferred groups of compounds are those of the formulae I 1 to I 8

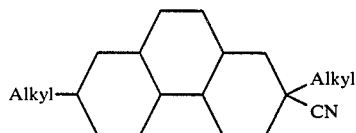

I1

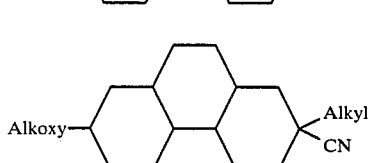

I2

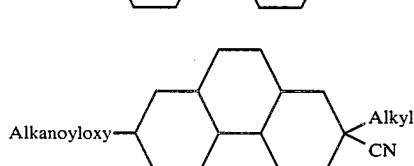

I3

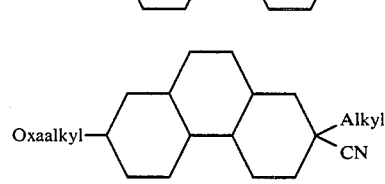

I4

I5

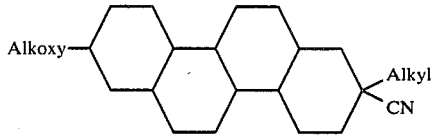

I6

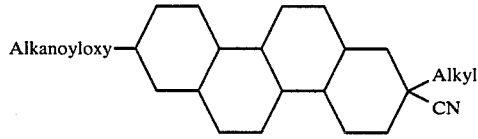

I7

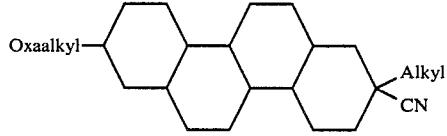

I8 wherein alkyl, alkoxy, alkanoyloxy and oxaalkyl independently of one another are each linear groups having 1–12, in particular 2–7, C atoms.

The compounds of the partial formulae Ia and Ib possess several centers of asymmetry. When prepared, therefore, they can be obtained in the form of racemates or, if optically active starting materials are used, can also be obtained in an optically active form. Optically active enantiomers of the formula I can, for example, be used with advantage as additives for ferroelectric, smectic phases. If mixtures of racemates are produced, the individual racemates can be isolated therefrom in a pure form, for example by recrystallizing from inert solvents the racemates themselves or diastereomeric derivatives thereof.

However, it is advantageous to conduct the synthesis in such a manner that the preferred racemates of the configurations Iaa or Iba

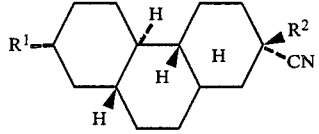

Iaa

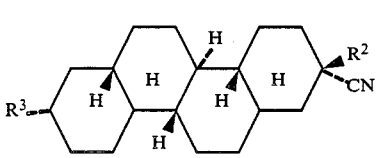

Iba wherein the substituents $R^1$ and $R^2$ or $R^2$ and $R^3$ are in an equatorial position and the CN group is in each case in an axial position are predominantly or exclusively formed.

The compounds of the formula I can be prepared by methods which are in themselves known, such as are described in the literature (for example in the standard works, such as Houben-Weyl, Methoden der Organischen Chemie ("Methods of Organic Chemistry"), Georg-Thieme-Verlag, Stuttgart), specifically under reaction conditions which are known and suitable for the reactions mentioned. In this respect it is also possible to make use of variants which are in themselves known but are not mentioned here.

If desired, the starting materials can also be formed in situ in such a way that they are not isolated from the reaction mixture, but are immediately reacted further to give the compounds of the formula I.

Thus the compounds of the formula I can be prepared by reacting a compound of the formula I wherein $R^2$ is H with a compound of the formula II $$R^2-X \qquad II$$

wherein
X is Cl, Br, I, OH or a reactive esterified OH group and $R^2$ has the meaning indicated.

The preparation of the perhydrophenanthrenecarbonitriles is disclosed in German Offenlegungsschrift No. 3,148,448; the perhydrochrysenecarbonitriles can be prepared by corresponding processes.

The nitrile is preferably first converted into the corresponding carbanion by means of a strong base, such as NaH, $NaNH_2$, lithium diisopropylamide, piperidide or 2,5-diisopropylpiperidide or K tert.-butylate, preferably in an inert solvent, for example a hydrocarbon, such as toluene, an ether, such as THF or dioxane, an amide, such as DMF, a sulfoxide, such as dimethyl sulfoxide or a mixture of solvents of this type. After the addition of II (wherein X is different from OH), it is preferable to keep the temperature between $-30°$ and $100°$ for 0.5 to 16 hours. On the other hand, a reaction with II (X=OH) is preferably carried out in the presence of axodicarboxylic acid esters/triphenylphosphine in THF at temperatures between about $-30°$ and $+30°$.

The liquid crystal phases according to the invention comprise 2 to 25, preferably 3 to 15, components, including at least one compound of the formula I. The other constituents are preferably selected from the nematic or nematogenic substances, in particular the known substances, belonging to the classes of azoxybenzenes, benzylideneanilines, biphenyls, terphenyls, phenylbenzoates or cyclohexylbenzoates, phenyl or cyclohexyl cyclohexanecarboxylates, plhenylcyclohexanes, cyclohexylbiphenyls, cyclohexylcyclohexanes, cyclohexylnaphthalenes, 1,4-bis-cyclohexylbenzenes, 4,4'-biscyclohexylbiphenyls, phenylpyrimidines or cyclohexylpyrimidines, phenyldioxanes or cyclohexyldioxanes, phenyl-1,3-dithianes or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes and substituted cinnamic acids.

The most important compounds which are suitable as constituents of liquid crystal phases of this type can be characterized by means of the formula II $$R'-L-G-E-R'' \qquad II$$

wherein L and E are each a carbocyclic or heterocyclic ring system belonging to the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene, quinazoline and tetrahydroquinazoline, G is

| —CH=CH— | —N(O)=N— |
| —CH=CY— | —CH=N(O)— |
| —C≡C— | —$CH_2$—$CH_2$— |
| —CO—O— | —$CH_2$—O— |
| —CO—S— | —$CH_2$—S— |
| —CH=N— | —COO—Phe—COO— | or a C—C single bond, Y is halogen, preferably chlorine, or —CN, and R' and R'' are alkyl, alkoxy, alkanoyloxy or alkoxycarbonyloxy having up to 18, preferably up to 8, carbon atoms, or one of these radicals is also CN, NC, $NO_2$, $CF_3$, F, Cl or Br.

In most of these compounds R' and R'' are different from one another and one of these radicals is in most cases an alkyl or alkoxy group. Other variants of the substituents intended are also customary, however. Many substances of this type or mixtures thereof are commercially available. All these substances can be prepared by methods known from the literature.

The phases according to the invention contain about 0.1 to 99%, preferably 10 to 95%, of one or more compounds of the formula I.

Dielectrics according to the invention containing 0.1 to 40%, preferably 0.5 to 30%, of one or more compounds of the formula I are also preferred.

The preparation of the dielectrics according to the invention is effected in a manner which is in itself customary. As a rule, the components are dissolved in one another, preferably at an elevated temperature.

It is possible, by means of suitable additives, to modify the liquid crystal dielectrics according to the invention in such a way that they can be used in all hitherto disclosed types of liquid crystal display elements.

Additives of this type are known to those skilled in the art and are described in detail in the literature. For example, it is possible to add conducting salts, preferably ethyldimethyldodecylammonium 4-hexyloxybenzoate, tetrabutylammonium tetraphenylboranate or complex salts of crown ethers (cf, for example, I. Haller et al., Mol. Cryst. Liq. Cryst. Volume 24, pages 249–258 (1973)) in order to improve the conductivity, to add dichroic dyestuffs in order to prepare colored guest-host systems or to add substances for modifying the dielectric anisotropy, the viscosity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

"Customary working up" means: water is added, the mixture is extracted with methylene chloride, the phases are separated, the organic phase is dried and evaporated and the product is purified by crystallization and/or chromatography.

EXAMPLE 1

30 g of 2β-cyano-7α-n-hexyl-4aβ-H-4bα-H-8aβ-H-10aα-H-perhydrophenanthrene (synthesis described in German Offenlegungsschrift No. 3,148,448) and 36 g of n-propyl bromide are dissolved in 100 ml of toluene, 4.3 g of NaNH$_2$ (50% mixture with toluene) is added and the mixture is boiled for 5 hours. 2α-Cyano-2β-n-propyl-7α-n-hexyl-4aβ-H-4bα-H-8aβ-H-10aα-H-perhydrophenanthrene is obtained after working up in the customary manner.

The following are obtained analogously by alkylating the corresponding nitriles (in the text which follows 4aβ-H-4bα-H-8aβ-H-10aα-H-perhydrophenanthrene is abbreviated to "perhydrophenanthrene"):

2α-Cyano-2β-propyl-7α-ethyl-perhydrophenanthrene
2α-Cyano-2β-propyl-7α-propyl-perhydrophenanthrene
2α-Cyano-2β-propyl-7α-butyl-perhydrophenanthrene
2α-Cyano-2β-propyl-7α-pentyl-perhydrophenanthrene
2α-Cyano-2β-propyl-7α-heptyl-perhydrophenanthrene
2α-Cyano-2β-ethyl-7α-ethyl-perhydrophenanthrene
2α-Cyano-2β-ethyl-7α-propyl-perhydrophenanthrene
2α-Cyano-2β-ethyl-7α-butyl-perhydrophenanthrene
2α-Cyano-2β-ethyl-7α-pentyl-perhydrophenanthrene
2α-Cyano-2β-ethyl-7α-heptyl-perhydrophenanthrene
2α-Cyano-2β-butyl-7α-ethyl-perhydrophenanthrene
2α-Cyano-2β-butyl-7α-propyl-perhydrophenanthrene
2α-Cyano-2β-butyl-7α-butyl-perhydrophenanthrene
2α-Cyano-2β-butyl-7α-pentyl-perhydrophenanthrene
2α-Cyano-2β-butyl-7α-heptyl-perhydrophenanthrene
2α-Cyano-2β-pentyl-7α-ethyl-perhydrophenanthrene
2α-Cyano-2β-pentyl-7α-propyl-perhydrophenanthrene
2α-Cyano-2β-pentyl-7α-butyl-perhydrophenanthrene
2α-Cyano-2β-pentyl-7α-pentyl-perhydrophenanthrene
2α-Cyano-2β-pentyl-7α-heptyl-perhydrophenanthrene
2α-Cyano-2β-hexyl-7α-ethyl-perhydrophenanthrene
2α-Cyano-2β-hexyl-7α-propyl-perhydrophenanthrene
2α-Cyano-2β-hexyl-7α-butyl-perhydrophenanthrene
2α-Cyano-2β-hexyl-7α-pentyl-perhydrophenanthrene
2α-Cyano-2β-hexyl-7α-heptyl-perhydrophenanthrene
2α-Cyano-2β-heptyl-7α-ethyl-perhydrophenanthrene
2α-Cyano-2β-heptyl-7α-propyl-perhydrophenanthrene
2α-Cyano-2β-heptyl-7α-butyl-perhydrophenanthrene
2α-Cyano-2β-heptyl-7α-pentyl-perhydrophenanthrene
2α-Cyano-2β-heptyl-7α-heptyl-perhydrophenanthrene
2α-Cyano-2β-pentyl-7α-methoxy-perhydrophenanthrene
2α-Cyano-2β-pentyl-7α-ethoxy-perhydrophenanthrene
2α-Cyano-2β-pentyl-7α-propoxy-perhydrophenanthrene
2α-Cyano-2β-pentyl-7α-butoxy-perhydrophenanthrene
2α-Cyano-2β-pentyl-7α-propionyloxy-perhydrophenanthrene
2α-Cyano-2β-pentyl-7α-butyryloxy-perhydrophenanthrene
2α-Cyano-2β-pentyl-7α-pentanoyloxy-perhydrophenanthrene
2α-Cyano-2β-pentyl-7α-2-oxabutyl-perhydrophenanthrene
2α-Cyano-2β-pentyl-7α-3-oxabutyl-perhydrophenanthrene

EXAMPLE 2

3.4 g of 2β-cyano-8α-n-pentyl-4aβ-H-4bα-H-10aα-H-10bβ-H-12aα-H-perhydrochrysene (synthesis described in German Patent Application No. P 3,426,039) and 3.6 g of n-propyl bromide are dissolved in 15 ml of toluene, 0.4 g of NaNH$_2$ (50% mixture with toluene) is added and the mixture is boiled for 6 hours. 2α-Cyano-2β-n-propyl-8α-n-pentyl-4aβ-H-4bα-H-10aα-H-10bβ-H-12aα-H-perhydrochrysene is obtained after working up in the customary manner.

The following are obtained analogously by alkylating the corresponding nitriles (in the text which follows 4aβ-H-4bα-H-10aα-H-10bβ-H-12aα-H-perhydrochrysene is abbreviated to "perhydrochrysene"):

2α-Cyano-2β-propyl-7α-ethyl-perhydrochrysene
2α-Cyano-2β-propyl-7α-propyl-perhydrochrysene
2α-Cyano-2β-propyl-7α-butyl-perhydrochrysene
2α-Cyano-2β-propyl-7α-pentyl-perhydrochrysene
2α-Cyano-2β-propyl-7α-heptyl-perhydrochrysene
2α-Cyano-2β-ethyl-7α-ethyl-perhydrochrysene
2α-Cyano-2β-ethyl-7α-propyl-perhydrochrysene
2α-Cyano-2β-ethyl-7α-butyl-perhydrochrysene
2α-Cyano-2β-ethyl-7α-pentyl-perhydrochrysene
2α-Cyano-2β-ethyl-7α-heptyl-perhydrochrysene
2α-Cyano-2β-butyl-7α-ethyl-perhydrochrysene
2α-Cyano-2β-butyl-7α-propyl-perhydrochrysene
2α-Cyano-2β-butyl-7α-butyl-perhydrochrysene
2α-Cyano-2β-butyl-7α-pentyl-perhydrochrysene
2α-Cyano-2β-butyl-7α-heptyl-perhydrochrysene
2α-Cyano-2β-pentyl-7α-ethyl-perhydrochrysene
2α-Cyano-2β-pentyl-7α-propyl-perhydrochrysene
2α-Cyano-2β-pentyl-7α-butyl-perhydrochrysene
2α-Cyano-2β-pentyl-7α-pentyl-perhydrochrysene
2α-Cyano-2β-pentyl-7α-heptyl-perhydrochrysene
2α-Cyano-2β-hexyl-7α-ethyl-perhydrochrysene
2α-Cyano-2β-hexyl-7α-propyl-perhydrochrysene
2α-Cyano-2β-hexyl-7α-butyl-perhydrochrysene
2α-Cyano-2β-hexyl-7α-pentyl-perhydrochrysene 2α-Cyano-2β-hexyl-7α-heptyl-perhydrochrysene
2α-Cyano-2β-heptyl-7α-ethyl-perhydrochrysene
2α-Cyano-2β-heptyl-7α-propyl-perhydrochrysene
2α-Cyano-2β-heptyl-7α-butyl-perhydrochrysene
2α-Cyano-2β-heptyl-7α-pentyl-perhydrochrysene
2α-Cyano-2β-heptyl-7α-heptyl-perhydrochrysene
2α-Cyano-2β-pentyl-7α-methoxy-perhydrochrysene
2α-Cyano-2β-pentyl-7α-ethoxy-perhydrochrysene
2α-Cyano-2β-pentyl-7α-propoxy-perhydrochrysene
2α-Cyano-2β-pentyl-7α-butoxy-perhydrochrysene
2α-Cyano-2β-pentyl-7α-propionyloxy-perhydrochrysene
2α-Cyano-2β-pentyl-7α-butyryloxy-perhydrochrysene
2α-Cyano-2β-pentyl-7α-pentanoyloxy-perhydrochrysene
2α-Cyano-2β-pentyl-7α-2-oxabutyl-perhydrochrysene
2α-Cyano-2β-pentyl-7α-3-oxabutyl-perhydrochrysene The following are examples of dielectrics according to the invention containing at least one compound of the formula I:

EXAMPLE A

A mixture of
10% of 2α-cyano-2β-propyl-7α-hexyl-perhydrophenanthrene,
24% of 2β-cyano-2α-heptyl-6β-propyltrans-decalin,
22% of 2β-cyano-2α-propyl-6β-pentyltrans-decalin,
21% of 2β-cyano-2α-,6β-dipentyltrans-decalin,
13% of 2β-cyano-2α-propyl-6β-heptyltrans-decalin and
10% of 4-(trans-4-pentylcyclohexyl)-4'-(trans-4-propylcyclohexyl)-biphenyl
is prepared.

EXAMPLE B 2 parts by weight of the blue dyestuff 4,8-diamino-1,5-dihydroxy-2-p-methoxyphenylanthraquinone are dissolved in 98 parts by weight of the mixture according to Example A.

EXAMPLE C

A mixture of
- 30% of 2α-cyano-2β-propyl-7α-hexyl-perhydrophenanthrene,
- 11% of p-ethoxyphenyl trans-4-propylcyclohexanecarboxylate,
- 9% of 4-(trans-4-pentylcyclohexyl)-4'-(trans-4-propylcyclohexyl)-biphenyl,
- 28% of 4-ethyl-2'-fluoro-4'-(trans-4-pentylcyclohexyl)-biphenyl and
- 22% of trans-1-(p-ethoxyphenyl)-4-propylcyclohexane is prepared.

EXAMPLE D

A mixture of
- 22% of 2β-cyano-2α-heptyl-6β-propyltrans-decalin,
- 20% of 2β-cyano-2α,6β-dipentyltrans-decalin,
- 18% of trans-4-propylcyclohexyl trans-4-pentylcyclohexanecarboxylate,
- 0.5% of 2α-cyano-2β-propyl-7α-hexyl-perhydrophenanthrene,
- 9.5% of 4-(trans-4-pentylcyclohexyl)-4'-(trans-4-propylcyclohexyl)-biphenyl and
- 30% of 4-ethyl-2'-fluoro-4'-(trans-4-pentylcyclohexyl)-biphenyl is prepared.

EXAMPLE E

A mixture of
- 17% of 2α-cyano-2β-propyl-8α-pentyl-perhydrochrysene,
- 43% of trans-4-propylcyclohexyl trans-4-propylcyclohexanecarboxylate,
- 16% of trans-4-propylcyclohexyl trans-4-pentylcyclohexanecarboxylate and
- 17% of 4-butyl-2-cyanophenyl p-(trans-4-propylcyclohexyl)-benzoate is prepared.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbonitrile of the formula

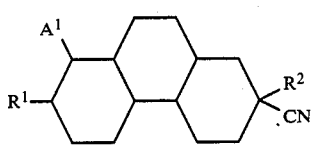

wherein
each of $R^1$ and $R^2$ independently is alkyl of 1–12 C atoms, or alkyl of 1–12 C atoms wherein one or two non-adjacent $CH_2$ groups are replaced by —O—, —O—CO—, —CO—O— or —CH=CH—, and $A^1$ is H or

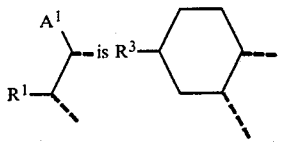

wherein
$R^3$ is one of the groups defined for $R^1$.

2. A compound of claim 1 of the formula

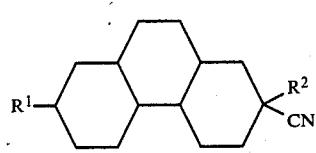

3. A compound of claim 1 of the formula

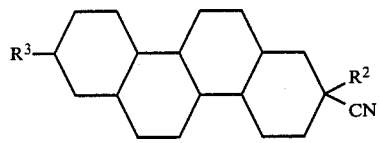

4. A compound of claim 1 wherein each of $R^1$ and $R^3$ independently is alkyl, alkoxy or oxaalkyl and $R^2$ is alkyl.

5. A compound of claim 1 of the formula

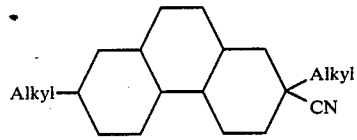

6. A compound of claim 1 of the formula

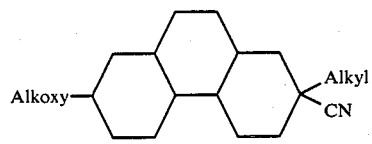

7. A compound of claim 1 of the formula

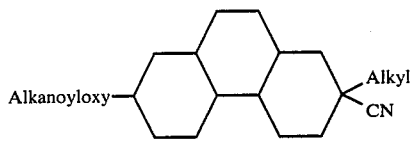

8. A compound of claim 1 of the formula

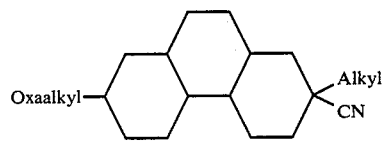

9. A compound of claim 1 of the formula

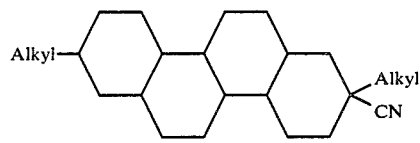

10. A compound of claim 1 of the formula

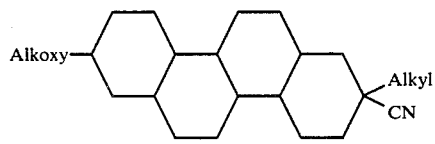

11. A compound of claim 1 of the formula

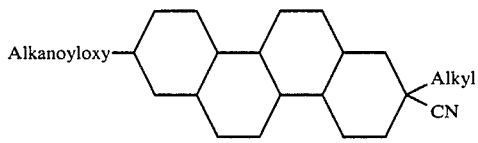

12. A compound of claim 1 of the formula

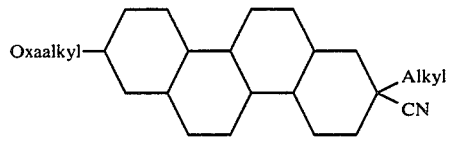

13. A compound of claim 1 of the formula

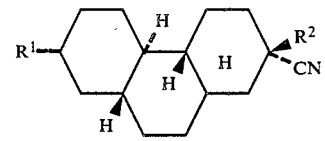

wherein $R^1$ and $R^2$ are in equatorial positions and CN is axial.

14. A compound of claim 1 of the formula

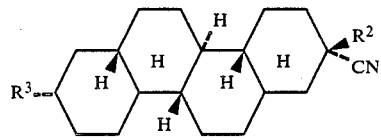

wherein $R^2$ and $R^3$ are in equatorial positions and CN is axial.

15. A liquid crystal phase having at least two liquid crystal components wherein at least one component is a compound of claim 1.

16. In a liquid crystal display element comprising a liquid crystal phase, the improvement wherein the phase is one of claim 15.

17. In an electrooptical display element comprising a liquid crystal dielectric, the improvement wherein the dielectric is a phase of claim 15.

* * * * *